United States Patent
Zhang et al.

(10) Patent No.: US 9,907,310 B2
(45) Date of Patent: Mar. 6, 2018

(54) HIGH RESIDUAL EFFECT AND LOW OFF-SITE MOVEMENT AUXIN HERBICIDE FORMULATIONS

(71) Applicant: Monsanto Technology LLC, St. Louis, MO (US)

(72) Inventors: Junhua Zhang, St. Louis, MO (US); Daniel R. Wright, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 14/150,004

(22) Filed: Jan. 8, 2014

(65) Prior Publication Data

US 2014/0200139 A1    Jul. 17, 2014

Related U.S. Application Data

(60) Provisional application No. 61/751,476, filed on Jan. 11, 2013.

(51) Int. Cl.
  *A01N 57/20*    (2006.01)
  *A01N 39/04*    (2006.01)
  *A01N 43/40*    (2006.01)
  *A01N 37/40*    (2006.01)

(52) U.S. Cl.
  CPC ............ *A01N 57/20* (2013.01); *A01N 37/40* (2013.01); *A01N 39/04* (2013.01); *A01N 43/40* (2013.01)

(58) Field of Classification Search
  None
  See application file for complete search history.

(56) References Cited

U.S. PATENT DOCUMENTS

| | | | |
|---|---|---|---|
| 4,459,150 A * | 7/1984 | Hatton et al. | 504/282 |
| 4,589,988 A * | 5/1986 | Rieck | C11D 3/001 423/332 |
| 4,849,006 A | 7/1989 | Knudson, Jr. | |
| 5,201,933 A * | 4/1993 | Miller | A01N 37/40 504/104 |
| 5,462,915 A * | 10/1995 | Curtis et al. | 504/323 |
| 5,670,454 A | 9/1997 | Grossman et al. | |
| 5,883,046 A | 3/1999 | Luteria | |
| 7,030,062 B2 | 4/2006 | Nir et al. | |
| 2001/0054367 A1 | 12/2001 | Pearce, III et al. | |
| 2002/0193256 A1 | 12/2002 | Harris, Jr. | |
| 2004/0087447 A1 * | 5/2004 | Nir et al. | 504/211 |
| 2008/0207452 A1 | 8/2008 | Kramer et al. | |
| 2008/0207453 A1 | 8/2008 | Kramer et al. | |
| 2010/0331182 A1 * | 12/2010 | Zhang et al. | 504/128 |
| 2011/0203013 A1 | 8/2011 | Peterson et al. | |
| 2012/0142532 A1 | 6/2012 | Wright et al. | |
| 2012/0309621 A1 * | 12/2012 | Lee | 504/133 |
| 2013/0109572 A1 * | 5/2013 | Pernak et al. | 504/206 |

FOREIGN PATENT DOCUMENTS

| | | |
|---|---|---|
| EP | 1974609 A1 | 10/2008 |
| WO | 9817113 A1 | 4/1998 |

OTHER PUBLICATIONS

Behrens et al. J Chem Phys vol. 115, No. 14, pp. 6716-6721; publication year: 2001.*
English Machine Translation of Patel (EP 1974609; publication date: Jan. 10, 2008). [retrieved on Apr. 27, 2016] retrieved from the internet: www.espacente.com.*
Biesaga, M., et al., "Comparison of Different Sorbents for Solid-Phase Extyraction of Phenoxyalkanoic Acid Herbicides," 2005, Michrochim Acta, 150:317-322.
Biesaga, M., et al., "The Evaluation of Carbon Nanotubes as a Sorbent for Dicamba Herbicide," 2006, J Spt Sci, 29:2241-2244.
Peruzzi, M., et al., "Determinatiomn of Phenoxyalkanoic Acids and Other Herbicides at the ng/ml Level in Water by Solid-Phase Extraction with Poly(divinylbenzene-co-N-vinylpyrrolidone) Sorbent and High-Performance Liquid Chromatography-Diode-Array Detection," 2000, J Chromatogr, 867:169-175.
Definition of PolyDADMAC, Wikipedia, downloaded May 2, 2012, 2 pages.
Poly(diallyldimethylammonium chloride) solution, CAS No. 26062-79-3, Sigma-Adrich Product Catalog, downloaded May 2, 2012, 3 pages.
Product Information Sheet, AERODISP W7730N, Evonik Industries AG, Jun. 2012, 2 pages.
International Search Report and Written Opinion issued in PCT/US2014/010594, dated Apr. 25, 2014, 13 pages.

* cited by examiner

*Primary Examiner* — Johann R Richter
*Assistant Examiner* — Katherine Peebles
(74) *Attorney, Agent, or Firm* — Senniger Powers LLP; Erin C. Robert (57) ABSTRACT

The present invention generally relates to high residual effect and/or low off-site movement anionic herbicide formulations and, more particularly, auxin herbicide formulations. Generally, the formulations of the present invention include an anionic herbicide (e.g., an auxin herbicide), a particulate sorbent (e.g., silica), a cationic surfactant, and water.

21 Claims, 4 Drawing Sheets

HIGH RESIDUAL EFFECT AND LOW OFF-SITE MOVEMENT AUXIN HERBICIDE FORMULATIONS

REFERENCE TO RELATED APPLICATION

This application claims the benefit of U.S. Provisional Application Ser. No. 61/751,476, filed Jan. 11, 2013, the entire contents of which are incorporated herein by reference.

FIELD OF THE INVENTION

The present invention generally relates to high residual effect and/or low off-site movement anionic herbicide formulations and, more particularly, auxin herbicide formulations. Generally, the formulations of the present invention include an anionic herbicide (e.g., an auxin herbicide), a particulate sorbent (e.g., silica), a cationic surfactant, and water.

BACKGROUND OF THE INVENTION

Auxin herbicides have proven to be effective and highly beneficial for control of unwanted plants. Auxin herbicides include 2,4-D (2,4-dichlorophenoxyacetic acid), 2,4-DB (4-(2,4-dichlorophenoxy)butanoic acid), dichloroprop (2-(2,4-dichlorophenoxy)propanoic acid), MCPA ((4-chloro-2-methylphenoxy)acetic acid), MCPB (4-(4-chloro-2-methylphenoxy)butanoic acid), aminopyralid (4-amino-3,6-dichloro-2-pyridinecarboxylic acid), clopyralid (3,6-dichloro-2-pyridinecarboxylic acid), fluroxypyr ([(4-amino-3,5-dichloro-6-fluoro-2-pyridinyl)oxy]acetic acid), triclopyr ([(3,5,6-trichloro-2-pyridinyl)oxy]acetic acid), diclopyr, mecoprop (2-(4-chloro-2-methylphenoxy)propanoic acid) and mecoprop-P, dicamba (3,6-dichloro-2-methoxybenzoic acid), picloram (4-amino-3,5,6-trichloro-2-pyridinecarboxylic acid), quinclorac (3,7-dichloro-8-quinolinecarboxylic acid), aminocyclopyrachlor (6-amino-5-chloro-2-cyclopropyl-4-pyrimidinecarboxylic acid), agriculturally acceptable salts of any of these herbicides, racemic mixtures and resolved isomers thereof, and mixtures thereof. Dicamba has proven to be a particularly effective auxin herbicide and is typically formulated as the sodium, dimethylamine, isopropylamine or diglycolamine salt.

One problem associated with auxin herbicides is loss of their herbicidal efficacy through dilution in ground water. In particular, this problem involves leaching of the auxin herbicide by ground water into lower soil layers. Auxin herbicides act in controlling unwanted plants by passing through the roots or stem of the plants. Accordingly, leaching of the herbicide into the lower soil layers reduces herbicidal efficacy. In addition, one benefit of auxin herbicides generally is providing efficacy over a relatively long period of time. Auxin herbicidal formulations are known as having a relatively high residual effect. However, dilution in ground water and leaching of the auxin herbicide into lower soil layers undermines the residual effect of auxin herbicide formulations. Thus, a need exists for an auxin herbicide formulation that avoids the problem of leaching and provides a relatively high residual effect.

Off-site movement is also often associated with dicamba and other auxin herbicides. Under certain conditions of application, dicamba can migrate from the application site to adjacent crop plants, such as soybeans and cotton, where contact damage to sensitive plants can occur. An additional need exists for auxin herbicide formulations that provide reduced off-site movement.

A further need exists for an auxin herbicide formulation that is suitable for use in connection with other herbicides (e.g., glyphosate) along with the auxin herbicide that also addresses the above-noted issues.

SUMMARY OF THE INVENTION

Generally, in various embodiments, the present invention is directed to aqueous herbicidal formulations, the formulations comprising (i) an anionic herbicide, (ii) a particulate sorbent, and (iii) a cationic surfactant.

In various such embodiments, the cationic surfactant is bonded to the particulate sorbent and the anionic herbicide is bonded to the cationic surfactant bound to the particulate sorbent; the particulate sorbent has a silica content of at least about 50 wt. %; and the concentration of anionic herbicide is at least about 0.1 wt % a.e.

In various other embodiments, the formulation comprises dicamba, particulate silica, and a cationic surfactant; the cationic surfactant is bonded to the particulate silica and dicamba is bonded to the cationic surfactant bound to the silica particles; the formulation further comprising glyphosate.

In still further embodiments, the formulation comprises an auxin herbicide, a particulate sorbent, and a cationic surfactant; the cationic surfactant is bonded to the particulate sorbent and the auxin herbicide is bonded to the cationic surfactant bound to the particulate sorbent; and the auxin herbicide concentration is at least about 0.1 wt. %.

The present invention is further directed to adjuvants for aqueous herbicidal formulations, the adjuvants comprising silica particles and a cationic surfactant; the cationic surfactant is bonded to the silica particles, and the adjuvant has a silica ($SiO_2$) content of at least about 20 wt. %.

The present invention is still further directed to methods for controlling weeds in a field of crop plants, the method comprising applying an aqueous herbicidal formulation of the present invention to the field in an herbicidally effective amount.

The present invention is also directed to methods for improving the residual effectiveness of an anionic herbicide. In various such embodiments, the method comprises combining an anionic herbicide, a particulate sorbent, a cationic surfactant, and water, thereby forming an aqueous herbicidal formulation wherein the cationic surfactant is bonded to the particulate sorbent and the anionic herbicide is bonded to the cationic surfactant bound to the particulate sorbent.

Other objects and features will be in part apparent and in part pointed out hereinafter.

DETAILED DESCRIPTION OF THE PREFERRED EMBODIMENTS

The present invention provides herbicidal formulations exhibiting advantageous herbicidal efficacy, in particular extended residual effect. Additionally or alternatively, the formulations of the present invention provide reduced off-site movement. It is currently believed that the formulations of the present invention provide extended residual effect by virtue of reduced leaching of the herbicide by ground water. This reduced leaching, and resulting extended residual effect, is provided by the structure, or arrangement of the herbicide (i.e., anionic herbicide) and other components of the formulation. In particular, the formulations of the present invention generally include a particulate sorbent, a cationic surfactant, and an anionic herbicide. The cationic surfactant is bonded to the particulate sorbent, and the anionic herbicide is bonded to the cationic surfactant bonded to the particulate sorbent. In various preferred embodiments, the anionic herbicide is an auxin herbicide and, therefore, the formulation includes an auxin herbicide bonded to the cationic surfactant.

The nature of the attraction or bond between the cationic surfactant and the particulate sorbent is currently believed to contribute to the advantageous properties of the formulations. In particular, it is currently believed that the bonding or attraction between the cationic surfactant and the particulate sorbent is an electrostatic attraction between these two components based on regions of positive charge of the cationic surfactant and regions of negative charge at the surface of the particulate sorbent. This bond or attraction is strong enough such that the cationic surfactant is retained to a suitable degree to reduce leaching and/or off-site movement of the anionic (auxin) herbicide, but not so strong as to prevent release of the anionic (auxin) herbicide from the structure. The anionic (auxin) herbicide (e.g., dicamba) is released from the particulate sorbent along with the cationic surfactant in a herbicidally active form.

As detailed below, in various preferred embodiments the particulate sorbent comprises silica and the cationic surfactant is bound to the silica by an electrostatic attraction to negatively charged regions of the silica. In this manner, the particulate silica sorbent is properly referred to as a "functionalized silica" or "physically bonded silica." This is in contrast to chemically modified silica where the silica forms a different chemical entity with a chemical modifying group.

It is currently believed that in various embodiments at least a portion of the cationic surfactant bonded to the sorbent is present in the form of a micelle structure, or micelle. In particular, it is currently believed that bonds between the hydrophobic tails of the cationic surfactant form and retain a micelle structure. The more hydrophobic the tail, the stronger the attraction between the hydrophobic tails of the cations and the stronger the micelle structure. Hydrophobicity of the tails generally increases as carbon chain length increases. Accordingly, in various preferred embodiments as detailed elsewhere herein, the cationic surfactant includes at least one carbon chain having up to, for example, 20 or 25 carbon atoms. The presence of the micelle structure is currently believed to contribute to bonding of the anionic (auxin) herbicide and retention of the anionic herbicide by or within the micelle structure. Accordingly, generally as the strength of the micelle structure increases, bonding and retention of the anionic (auxin) herbicide generally increases. However, since ultimately release of the anionic (auxin) herbicide is desired, preferably the strength of the micelle structure is not such as to prevent desired release of the anionic (auxin) herbicide.

I. Compositions

The formulations of the present invention generally include an anionic (auxin) herbicide, a particulate sorbent, and a cationic surfactant. As used herein, the term "anionic herbicide" generally refers to an herbicide that is capable of providing an herbicide anion in aqueous media. However, it is to be understood that the "anionic herbicide" may be present in the formulations of the present invention in either the acid form or anionic form. Generally, however, it is currently believed that at least a portion of the anionic herbicide is present in the anionic form (i.e., non-protonated) and not in the acid form or salt form.

As detailed above, in various preferred embodiments, the herbicide is an auxin herbicide. Accordingly, much of the following discussion focuses on compositions including auxin herbicides. However, it is to be understood that the following discussion also applies to herbicides other than auxin herbicides, including those listed below.

Auxin Herbicide

Generally, the auxin herbicide component is selected from the group consisting of 2,4-D (2,4-dichlorophenoxyacetic acid), 2,4-DB (4-(2,4-dichlorophenoxy)butanoic acid), dichloroprop (2-(2,4-dichlorophenoxy)propanoic acid), MCPA ((4-chloro-2-methylphenoxy)acetic acid), MCPB (4-(4-chloro-2-methylphenoxy)butanoic acid), aminopyralid (4-amino-3,6-dichloro-2-pyridinecarboxylic acid), clopyralid (3,6-dichloro-2-pyridinecarboxylic acid), fluroxypyr ([(4-amino-3,5-dichloro-6-fluoro-2-pyridinyl)oxy]acetic acid), triclopyr ([(3,5,6-trichloro-2-pyridinyl)oxy]acetic acid), diclopyr, mecoprop (2-(4-chloro-2-methylphenoxy)propanoic acid) and mecoprop-P, dicamba (3,6-dichloro-2-methoxybenzoic acid), picloram (4-amino-3,5,6-trichloro-2-pyridinecarboxylic acid), quinclorac (3,7-dichloro-8-quinolinecarboxylic acid), aminocyclopyrachlor (6-amino-5-chloro-2-cyclopropyl-4-pyrimidinecarboxylic acid), agriculturally acceptable salts of any of these herbicides, racemic mixtures and resolved isomers thereof, and mixtures thereof.

Typically, the anionic herbicide is an auxin herbicide salt selected from the group consisting of the sodium, potassium, ammonium, lithium, diammonium, monoethanolamine, diethanolamine, triethanolamine, triisopropanolamine, dimethylamine, diethylamine, triethylamine, methylamine, ethylamine, diglycolamine, propylamine, butylamine, pentylamine, hexylamine, heptylamine, octylamine, dodecylamine and decylamine salts, and combinations thereof.

In various embodiments, the auxin herbicide is selected from the group consisting of 2,4-D, 2,4-DB, MCPA, MCPB, aminocyclopyrachlor, aminopyralid, clopyralid, dichloroprop, fluroxypyr, triclopyr, diclopyr, mecoprop, mecoprop-P, dicamba, picloram and quinclorac, racemic mixtures and resolved isomers thereof, and combinations thereof.

In still further embodiments, the auxin herbicide is selected from the group consisting of dicamba, triclopyr, 2,4-D, and combinations thereof. In even further embodiments, the auxin herbicide is selected from the group consisting of dicamba, 2,4-D, and combinations thereof.

In various preferred embodiments, the auxin herbicide is dicamba. Dicamba is typically formulated as the monoethanolamine, diethanolamine, sodium, potassium, isopropylamine, diglycolamine, or dimethylamine salt. In various embodiments, dicamba is formulated as the monoethanolamine, diethanolamine, or potassium salt. In various preferred embodiments, the auxin herbicide ions are derived from the diglycolamine salt of dicamba.

Typically, the auxin (anionic) herbicide is in the form of a water-soluble auxin herbicide that provides auxin herbicide anions. Generally, the auxin herbicide has a water solubility of at least about 10 g/L at 25° C., at least about 25 g/L at 25° C., at least about 50 g/L at 25° C., at least about 75 g/L at 25° C. at 25° C., or at least about 100 g/L at 25° C. at 25° C.

Particulate Sorbent

Generally, the sorbent is a particulate sorbent and, more particularly, a silica-containing sorbent. Suitable particulate sorbents include those silicas generally known in the art. Such silicas include, for example, diatomaceous earth. Sorbents commonly referred to as silica often include other components, but typically have relatively high silica ($SiO_2$) content. Accordingly, typically the particulate sorbent has a silica content of at least about 50 wt %, or at least about 60 wt %. More typically, the sorbent typically has a silica content of at least about 70 wt %, at least about 80 wt %, at least about 90 wt %, or at least about 95 wt %.

Typically, the particulate sorbent has a Brunauer-Emmett-Teller (BET) surface area of from about 90 to about 300 $m^2/g$, from about 100 to about 250 $m^2/g$, or from about 100 to about 200 $m^2/g$.

Generally, the particulate sorbent has a particle size distribution such that at least about 50%, at least about 60%, at least about 70%, or at least about 80% by weight of the particulate sorbent has a particle size of from about 0.01 to about 200 µm, from about 0.01 to about 100 µm, from about 0.01 to about 50 µm, or from about 0.1 to about 20 µm.

Generally, the particulate sorbent has a negative charge at a pH of from about 2 to about 3.

Use of the particulate silica-containing sorbent (e.g., particulate sorbent having a relatively high silica content) provides various advantages. One advantage is its versatility of use with a wide variety of auxin herbicides and also its suitability for use in connection with herbicides that are often co-formulated with auxin herbicides (e.g., combining dicamba and glyphosate).

In addition, organoclays are known for use in connection with herbicidal formulations, and have proven effective for use in preparing dicamba formulations and are suitable for use in accordance with various embodiments of the present invention. However, certain issues have been observed when utilizing organoclays in herbicidal formulations. For example, organoclays may bind with, and thus deactivate, certain herbicides. In particular, this problem has been observed when attempting to formulate glyphosate in formulations utilizing an organoclay. Thus, in accordance with the present invention, the use of silica-containing sorbents and, more particularly, sorbents having relatively high silica content provide the advantage of avoiding this problem. But it is to be further noted that advantageous auxin herbicide formulations can be prepared utilizing organoclays and these formulations, although not required for their effectiveness, are also suitable for utilizing in combination with other herbicides, notably glyphosate.

Cationic Surfactant

As noted above, generally hydrophobic regions of the cationic surfactant form a micelle structure, which is bonded to the particulate sorbent and which retains the anionic (auxin) herbicide by attraction of the anionic herbicide to the micelle structure and/or regions of the cationic surfactant forming the micelle structure. Retention of the anionic herbicide in this manner contributes at least in part to the improvements in residual activity and/or reduced off-site movement provided by the compositions of the present invention.

Generally in accordance with the present invention a suitable proportion of cationic surfactant is included in order to provide a sufficient proportion of cationic surfactant bonded to the particulate sorbent to contribute to the desired performance (e.g., reduced leaching of the anionic herbicide).

Generally, the cationic surfactant bonded to the particulate sorbent is present in a proportion of at least about $1\times10^{-6}$ moles, at least about $1\times10^{-5}$ moles, or at least about $1\times10^{-4}$ moles cationic surfactant per unit particulate sorbent surface area (m/g).

Further generally, the cationic surfactant bonded to the particulate sorbent is present in a proportion of at least about $1\times10^{-4}$ moles, at least about $1\times10^{-3}$ moles, or at least about $1\times10^{-2}$ moles per gram particulate sorbent.

Likewise in accordance with the invention, preferably a suitable proportion of cationic surfactant is present with respect to the anionic (auxin) herbicide. Generally, the cationic surfactant is utilized in a proportion suitable to provide a sufficient amount of cationic surfactant, or sites for attraction between and/or bonding with the anionic herbicide. In this manner, the anionic herbicide is retained in the structure and the advantages of reduced leaching and/or off-site movement of the desired anionic herbicide loading is provided.

Generally, the molar ratio of the cationic surfactant to anionic herbicide is at least about 0.2:1, at least about 0.5:1, or at least about 1:1.

Typically, the molar ratio of the cationic surfactant to anionic herbicide is less than about 8:1, less than about 6:1, or less than about 4:1.

Thus, in various embodiments, the molar ratio of the cationic surfactant bonded to the anionic herbicide is from about 0.2:1 to about 8:1, from about 0.2:1 to about 6:1, or from about 0.2:1 to about 4:1, from about 0.5:1 to about 3:1, or from about 1:1 to about 2:1.

Suitable cationic surfactants include a variety of those known in the art. As detailed above, generally the cationic surfactant includes at least one carbon chain and as the length of the carbon chain increases, desired properties of the formulations are provided. In particular, as the length of the carbon chain increases the strength of the micelle structure increases and likewise improved retention of the anionic herbicide is provided. However, as detailed above, often it is preferred that the carbon chain length is not such that retention of the anionic herbicide is to a degree such that the active herbicide is not released from the micelle structure. Thus, generally, a cationic surfactant includes one or more R groups which are hydrocarbyl or substituted hydrocarbyl having from 1 to 25 carbon atoms, from 1 to 20 carbon atoms, or from 1 to 15 carbon atoms. In various embodiments, the cationic surfactant includes at least one R group which is a hydrocarbyl or substituted hydrocarbyl having from 5 to 25 carbon atoms or from 6 to 22 carbon atoms. More particularly, in various embodiments the cationic surfactants includes ions of the formulae described below.

In certain embodiments, the cationic surfactant comprises quaternary alkyl ammonium ions of the formula (I):

wherein $R^1$, $R^2$, $R^3$, and $R^4$ are hydrocarbyl or substituted hydrocarbyl having from 1 to 25 carbon atoms, from 1 to 20 carbon atoms, or from 1 to 15 carbon atoms.

In accordance with various such embodiments, $R^1$ is a hydrocarbyl or substituted hydrocarbyl having from 5 to 25 carbon atoms or from 6 to 22 carbon atoms.

Further in accordance with various such embodiments, $R^1$ is a hydrocarbyl or substituted hydrocarbyl having from 12 to 20 carbon atoms and $R^2$, $R^3$, and $R^4$ are methyl.

In various embodiments, $R^1$, $R^2$, $R^3$, and $R^4$ are ethyl.

In accordance with various other embodiments, the cationic surfactant comprises pyridinium ions of the formula (II):

(II)

wherein $R^{10}$ is hydrocarbyl or substituted hydrocarbyl having from 1 to 25 carbon atoms, from 1 to 20 carbon atoms, or from 10 to 20 carbon atoms.

In accordance with further embodiments, the cationic surfactant comprises bipyridinium ions of the formula (III):

(III)

wherein $R^{20}$ and $R^{25}$ are hydrocarbyl or substituted hydrocarbyl having from 1 to 25 carbon atoms, from 1 to 20 carbon atoms, or from 1 to 15 carbon atoms.

In accordance with various other embodiments, the cationic surfactant comprises pyrrolinium ions of the formula (IV):

(IV)

wherein $R^{30}$ is hydrocarbyl or substituted hydrocarbyl having from 1 to 25 carbon atoms, from 1 to 20 carbon atoms, or from 1 to 15 carbon atoms.

In other embodiments, the cationic surfactant comprises imidazolium ions of the formula (V):

(V)

wherein $R^{35}$ and $R^{40}$ are hydrocarbyl or substituted hydrocarbyl having from 1 to 25 carbon atoms, from 1 to 20 carbon atoms, or from 1 to 15 carbon atoms.

In further embodiments, the cationic surfactant comprises benzalkonium ions of the formula (VI):

(VI)

wherein $R^{45}$, $R^{50}$, $R^{55}$ are hydrocarbyl or substituted hydrocarbyl having from 1 to 25 carbon atoms, from 1 to 20 carbon atoms, or from 1 to 15 carbon atoms.

Water-Soluble Herbicides

As detailed above, the present invention is directed to formulations incorporating an anionic herbicide and, more particularly, an auxin herbicide. However, in various embodiments, the present invention is generally directed to formulations that incorporate a water-soluble herbicide (including certain of the auxin herbicides listed above) along with a particulate sorbent and a cationic surfactant.

In particular, in various embodiments, the water-soluble herbicide is selected from the group consisting of 2,4-D, aminopyralid, clopyralid, fluroxypyr, MCPA, and salts thereof; 2,4-DB salts, dichloroprop salts, MCPB salts, mecoprop salts, picloram salts, quinclorac salts, and triclopyr salts; and water soluble acids, salts and esters of acifluorfen, alloxydim, aminocarbazone, amidosulfuron, amitrole, asulam, azafenidin, azimsulfuron, beflubutamid, benazolin, bentazon, bensulfuron-methyl, bispyribac, bromacil, carbetamide, carfentrazone-ethyl, chlorimuron-ethyl, chlorsulfuron, cinosulfuron, clomazone, dalapon, dazomet, dicamba, dichlormid, diclofop, diclopyr, difenzoquat, deflufenzopyr, dimethachlor, dimethenamid, dimethipin, diquat dibromide, DNOC, DSMA, endothall, exasulfuron, flazasulfuron, floramsulfuron, florasulam, flucarbazone-sodium, flupropanate, fluthiacet, fomesafen, foramsulfuron, fosamine, glyphosate, glufosinate, glufosinate-P, hexazinone, imazamethabenz-methyl, imazamox, imazapic-ammonium, imazapyr, imazaquin-ammonium, imazethapyr-ammonium, iodosulfuron, mesotrione, metam, metamitron, metham, metosulam, metribuzin, metsulfuron-methyl, molinate, monolinuron, MSMA, water soluble salts of oleic acid, naptalam, oxasulfuron, paraquat dichloride, water-soluble salts of pelargonic acid, penoxsulam, prometon, propoxycarbazone-sodium, prosulfuron, pyrithiobac-sodium, quinmerac, rimsulfuron, sethoxydim, sulfosulfuron, TBA, tebuthiuron, terbacil, thifensulfuron-methyl, tralkoxydim, triasulfuron, tribenuron-methyl, triclopyr, and trifloxysulfuron; racemic mixtures and resolved isomers thereof; and mixtures thereof.

Co-Herbicides

In some embodiments of the present invention, the dicamba formulations of the present invention are used in the preparation of concentrate, tank mix or ready to use (RTU) formulations further comprising one or more additional co-herbicides. Co-herbicides include auxin herbicide salts other than dicamba salts (as previously described). Co-herbicides also include acetyl CoA carboxylase (ACCase) inhibitors, acetolactate synthase (ALS) or acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin transport inhibitors and nucleic acid inhibitors, salts and esters thereof, racemic mixtures and resolved isomers thereof, and combinations thereof.

Included within the scope of co-herbicides are racemic mixtures and resolved isomers. Typical cations for the co-herbicide salts of the present invention include potassium, MEA, DMA, IPA, trimethylsulfonium (TMS) diethylammonium (DEA), lithium, and ammonium. Typical anions for the formation of co-herbicide salts include chlorine, bromine, fluorine and acetate. Typical esters include methyl, ethyl, propyl, isopropyl, butyl, isobutyl, pentyl, isooctyl, ethylhexyl, ethoxyethyl, butoxyethyl, butoxypropyl and octanoate.

Examples of ACCase inhibitors include clethodim, clodinafop, fenoxaprop-P, fluazifop-P, quizalofop-P and sethoxydim. Examples of ALS or AHAS inhibitors include flumetsulam, imazamethabenz-m, imazamox, imazapic, imazapyr, imazaquin, imazethapyr, metsulfuron, prosulfuron and sulfosulfuron. Examples of photosystem I inhibitors include diquat and paraquat. Examples of photosystem II inhibitors include atrazine, cyanazine and diuron. Examples of PPO inhibitors include acifluorofen, butafenacil, carfentrazone-ethyl, flufenpyr-ethyl, fluthiacet, flumiclorac, flumioxazin, fomesafen, lactofen, oxadiazon, oxyflurofen and sulfentrazone. Examples of carotenoid biosynthesis inhibitors include aclonifen, amitrole, diflufenican and sulcotrione. Glyphosate is an EPSP inhibitor, glufosinate is a glutamine synthetase inhibitor and asulam is a dihydropteroate synthetase inhibitor. Examples of mitosis inhibitors include acetochlor, alachlor, dithiopyr, S-metolachlor and thiazopyr. Naptalam is an example of a auxin transport inhibitor. Examples of nucleic acid inhibitors include difenzoquat, fosamine, metham and pelargonic acid.

Particular examples of water-soluble herbicides suitable for use as co-herbicides include, without restriction, 2,4-D, aminopyralid, clopyralid, fluroxypyr, MCPA, and salts thereof; 2,4-DB salts, dichloroprop salts, MCPB salts, mecoprop salts, picloram salts, quinclorac salts, and triclopyr salts; and water soluble acids, salts and esters of acifluorfen, alloxydim, aminocarbazone, amidosulfuron, amitrole, asulam, azafenidin, azimsulfuron, beflubutamid, benazolin, bentazon, bensulfuron-methyl, bispyribac, bromacil, carbetamide, carfentrazone-ethyl, chlorimuron-ethyl, chlorsulfuron, cinosulfuron, clomazone, dalapon, dazomet, dicamba, dichlormid, diclofop, diclopyr, difenzoquat, deflufenzopyr, dimethachlor, dimethenamid, dimethipin, diquat dibromide, DNOC, DSMA, endothall, exasulfuron, flazasulfuron, floramsulfuron, florasulam, flucarbazone-sodium, flupropanate, fluthiacet, fomesafen, foramsulfuron, fosamine, glyphosate, glufosinate, glufosinate-P, hexazinone, imazamethabenz-methyl, imazamox, imazapic-ammonium, imazapyr, imazaquin-ammonium, imazethapyr-ammonium, iodosulfuron, mesotrione, metam, metamitron, metham, metosulam, metribuzin, metsulfuron-methyl, molinate, monolinuron, MSMA, water soluble salts of oleic acid, naptalam, oxasulfuron, paraquat dichloride, water-soluble salts of pelargonic acid, penoxsulam, prometon, propoxycarbazone-sodium, prosulfuron, pyrithiobac-sodium, quinmerac, rimsulfuron, sethoxydim, sulfosulfuron, TBA, tebuthiuron, terbacil, thifensulfuron-methyl, tralkoxydim, triasulfuron, tribenuron-methyl, triclopyr, and trifloxysulfuron; racemic mixtures and resolved isomers thereof; and mixtures thereof.

Examples of suitable water-insoluble herbicides include, without restriction, acetochlor, acifluorfen, aclonifen, alachlor, ametryn, anilofos, atrazine, azafenidin, benfluralin, bensulfuron-methyl, bensulide, benzofenap, bifenox, bromoxynil, butachlor, butroxydim, butylate, cafenstrole, chlomethoxyfen, chlorbromuron, chloridazon, chlornitrofen, chlorotoluron, chlorthal-dimethyl, chlorthiamid, cinmethylin, clethodim, clodinafop-propargyl, cloransulam-methyl, cyanazine, cycloate, cyclosulfamuron, cycloxydim, cyhalofop-butyl, desmedipham, desmetryn, dichlobenil, diclosulam, diflufenican, dimefuron, dimepiperate, dimethachlor, dinitramine, dinoterb, dithiopyr, diuron, EPTC, esprocarb, ethalfluralin, ethametsulfuron-methyl, ethofumesate, ethoxysulfuron, fenoxaprop-ethyl, fentrazamide, fluazifop-butyl, flucetosulfuron, fluchloralin, flufenacet, flufenpyr-ethyl, flumetsulam, flumiclorac-pentyl, flumioxazin, fluometuron, fluorochloridone, fluoroglycofen, flupyrsulfuron-methyl-sodium, fluridone, fluroxypyr-1-methylheptyl, flurtamone, fluthiacet-methyl, fomesafen, foramsulfuron, furyloxyfen, halosulfuron-methyl, haloxyfop-methyl, imazosulfuron, ioxynil, isoproturon, isoxaben, isoxaflutole, lactofen, lenacil, linuron, mefenacet, metazachlor, methabenzthiazuron, metobromuron, metolachlor, metosulam, metoxuron, metribuzin, molinate, monolinuron, napropamide, niocosulfuron, nitrofen, nitrofluorfen, norflurazon, oryzalin, oxadiargyl, oxadiazon, oxasulfuron, oxyfluorfen, pebulate, pelargonic acid, pendimethalin, phenmedipham, pretilachlor, primisulfuron-methyl, prodiamine, prometon, prometryn, propachlor, propanil, propaquizafop, propisochlor, propyzamide, prosulfocarb, pyraflufen-ethyl, pyrazolynate, pyrazon, pyrazosulfuron-ethyl, pyrazoxyfen, pyribenoxim, pyridate, quinclorac, quinmerac, quizalofop-ethyl, rimsulfuron, siduron, simazine, simetryn, sulcotrione, sulfentrazone, sulfometuron, terbacil, terbumeton, terbuthylazine, terbutryn, thenylchlor, thiazopyr, thiobencarb, triallate, trietazine, trifluralin, triflusulfuron-methyl, and vernolate, agriculturally acceptable salts or esters of any of these herbicides, racemic mixtures and resolved isomers thereof, and combinations thereof.

Some preferred water-soluble herbicides suitable as co-herbicides include 2,4-D and salts thereof, acifluorfen salts, carfentrazone-ethyl, fomesafen salts, glyphosate and salts thereof, glufosinate and salts thereof, imazamethabenz and salts and esters thereof, imazamox and salts and esters thereof, imazapic and salts and esters thereof, imazapyr and salts and esters thereof, imazaquin and salts and esters thereof, imazethapyr and salts and esters thereof, mecoprop salts, triclopyr salts, racemic mixtures and resolved isomers thereof, and combinations thereof. Some preferred water-insoluble herbicides include acetochlor, alachlor, atrazine, azafenidin, bifenox, butachlor, butafenacil, diuron, dithiopyr, flufenpyr-ethyl, flumiclorac-pentyl, flumioxazin, fluoroglycofen, fluthiacet-methyl, lactofen, metazochlor, metolachlor (and S-metolachlor), oxadiargyl, oxadiazon, oxyfluorfen, pretilachlor, propachlor, propisochlor, pyraflufen-ethyl, sulfentrazone and thenylchlor, racemic mixtures and resolved isomers thereof, and combinations thereof.

II. Formulations

In various embodiments of the present invention, dicamba tank mix formulations are provided. The tank mix formulations typically contain from about 0.1 to about 50 g a.e./L, such as about 0.1, about 0.5, about 1, about 5, about 10, about 25 or about 50 g a.e./L dicamba, and ranges thereof.

In various other embodiments, dicamba concentrate formulations are provided. The concentrate formulations typically containing at least about 10 g a.e./L dicamba, such as from about 10 to about 800, from about 20 to about 750, from about 50 to about 750, from about 100 to about 750, from about 200 to about 600, from about 250 to about 550, from about 300 to about 450, from about 300 to about 400, from about 325 to about 375, or about 360 g a.e./L dicamba. For example, about 50, about 100, about 150, about 200, about 250, about 300, about 350, about 400, about 450, about 500, about 550, about 600, about 650, about 700, about 750, about 800, about 850 or about 885 g a.e./L, and ranges thereof.

In co-herbicide formulations, the weight ratio on an acid equivalent basis of the carboxylic acid herbicide amine salt to the total co-herbicide is typically no greater than about 50:1, for example, about 50:1, 25:1, 10:1, 5:1, 3:1, 2:1, 1:1, 1:2, 1:3, 1:5 or even about 1:10 and ranges thereof (e.g., from about 50:1 to about 1:10, from about 50:1 to about 1:5, from about 50:1 to about 1:1, from about 50:1 to about 3:1, from about 50:1 to about 5:1, from about 50:1 to about 10:1, from about 25:1 to about 1:1, or from about 25:1 to about 3:1, on an acid equivalent basis).

In accordance with these and other embodiments, the anionic herbicide (e.g., dicamba) is present at a concentration of from about 0.1 to about 80 wt. % a.e., from about 1 to about 60 wt. % a.e., from about 5 to about 60 wt. % a.e, from about 5 to about 50 wt % a.e., from about 10 to about 40 wt. % a.e., from about 10 to about 30 wt. % a.e., or from about 10 to about 20 wt. % a.e.

As noted above, in various embodiments, the formulation includes glyphosate along with dicamba. In accordance with such embodiments, typically glyphosate is present in either a tank-mix or concentrate formulation at one or more of the noted exemplary dicamba concentrations.

Anionic herbicides utilized in accordance with the present invention may be formulated with other conventional adjuvants, excipients or additives known to those skilled in the art. These other additives or ingredients may be introduced into the compositions of the present invention to provide or improve certain desired properties or characteristics of the formulated product. Hence, the herbicidal composition may further comprise one or more additional ingredients selected from, without limitation, surfactants, foam-moderating agents, preservatives or anti-microbials, antifreeze agents, solubility-enhancing agents, dispersants, stabilizers, dyes, and thickening agents. For example, in various embodiments, the herbicidal composition further comprises a surfactant selected from the group consisting of alkoxylated tertiary etheramines, alkoxylated quaternary etheramines, alkoxylated etheramine oxides, alkoxylated tertiary amines, alkoxylated quaternary amines, alkoxylated polyamines, sulfates, sulfonates, phosphate esters, alkyl polysaccharides, alkoxylated alcohols, and combinations thereof. The weight ratio of the anionic herbicide acid equivalent to surfactant can be readily determined by those skilled in the art (e.g., from about 1:1 to about 20:1, from about 2:1 to about 10:1 or from about 3:1 to about 8:1).

III. High Residual Effect and Reduced Off-Site Movement

As shown in the working examples appended hereto, testing utilizing formulations prepared in accordance with the present invention indicate improved residual effects at varying time intervals after treatment (e.g., at 7 days, 14 days, and even up to 28 days after treatment).

It is also currently believed that the data provided herein indicate reduced off-site movement of the formulations of the present invention.

Volatilization can be measured by means known to those skilled in the art such as distilling auxin herbicide concentrations and analyzing the distillation condensate and/or distilled composition for auxin content. Volatility can also be tested by passing a gas stream over auxin herbicide formulations into which the auxin herbicide volatilizes from the formulation; the gas stream can then be quantitatively analyzed for dicamba content by methods known in the art. Results of volatility testing are provided in the Examples submitted herewith.

The present invention is also directed to methods for improving the residual effectiveness of an anionic herbicide that generally comprises combining an anionic herbicide, a particulate sorbent, a cationic surfactant, and water. Combining these components provides an aqueous herbicidal formulation in which the cationic surfactant is bonded to the particulate sorbent and the anionic herbicide is bonded to the cationic surfactant bound to the particulate sorbent. In various embodiments, the particulate sorbent and cationic surfactant are initially present separately as an adjuvant (e.g., as a tank-mix additive or a tank-mix) that is combined with the anionic herbicide by either introducing the adjuvant into a tank, or vessel including the anionic herbicide or introducing the anionic herbicide into a tank, or vessel that includes the cationic surfactant/particulate sorbent adjuvant.

IV. Adjuvants

In certain embodiments, the present invention is directed to an adjuvant comprising silica particles and a cationic surfactant. The cationic surfactant is bonded to the silica particles and the adjuvant has an overall silica ($SiO_2$) content of at least about 20 wt. %, at least about 30 wt. %, at least about 40 wt. %, at least about 50 wt. %, or at least about 60 wt. %.

V. Methods of Use

In herbicidal methods of the present invention of using a formulation of the invention, an application mixture, typically comprising from about 0.1 to about 50 g a.e./L herbicide, is formed and then applied to the foliage of a plant or plants or an area where plants are to be planted at an application rate sufficient to give a commercially acceptable rate of weed control. Application mixtures are typically prepared from aqueous concentrate formulations by dilution with water to achieve the desired concentration. This application rate is usually expressed as amount of auxin herbicide per unit area treated, e.g., grams acid equivalent per hectare (g a.e./ha). Depending on plant species and growing conditions, the period of time required to achieve a commercially acceptable rate of weed control can be as short as a week or as long as three weeks, four weeks or 30 days. Typically a period of about two to three weeks is needed for the auxin herbicide to exert its full effect.

Application mixtures prepared in accordance with the present invention may be applied to the foliage of crop plants and/or unwanted plants in the proximity of crop plants. In some embodiments of the present invention, crop plants include, for example, corn, peanuts, potatoes, soybeans, canola, alfalfa, sugarcane, sugarbeets, peanuts, grain sorghum (milo), field beans, rice, sunflowers, wheat and cotton. In certain embodiments, the crop plant is selected from the group consisting of soybeans, cotton, peanuts, rice, wheat, canola, alfalfa, sugarcane, sorghum, and sunflowers. In various embodiments, the crop plant is selected from the group consisting of corn, soybean and cotton.

Crop plants include hybrids, inbreds, and transgenic or genetically modified plants having specific traits or combinations of traits including, without limitation, herbicide tolerance (e.g., resistance to glyphosate, glufosinate, dicamba, sethoxydim, etc.), *Bacillus thuringiensis* (Bt), high oil, high lysine, high starch, nutritional density, and drought resistance. In some embodiments, the crop plants are resistant to dicamba and/or glyphosate.

Genetically engineered crop plants of the present invention include, for example, cotton, soybeans, sugar beet, sugar cane, plantation crops, tobacco, rape, maize and rice. Examples of crops having herbicidal resistance given by a genetic engineering technique include corn, soybean and cotton having resistance to glyphosate (Roundup Ready®) and glufosinate (Liberty Link®). Other examples of herbicide resistant crop plants include dicamba, 2,4-D, dicamba or sethoxydim resistant corn, cotton and soybean; imidazolinone (imazethapyr and imazapyr) resistant corn (Imi-Corn®) and soybeans; and glyphosate and glufosinate resistant corn (SmartStax®).

In some embodiments of the present invention, dicamba (or a salt thereof) is combined with glyphosate co-herbicide (or a salt or ester thereof), the crop plant comprises a glyphosate-resistant trait and the crop plant is further either (i) a plant species not susceptible to auxin herbicides or (ii) comprises a dicamba resistant trait. Such compositions are useful to control (i) glyphosate susceptible plants and (ii) glyphosate resistant, but auxin susceptible, volunteer crop plants and/or weeds growing in a field of (iii) glyphosate and auxin resistant or tolerant crop plants.

The formulations of the present invention can be applied prior to planting of the crop plant, such as, for example, from about 2 to about 3 weeks before planting auxin-susceptible crop plants or crop plants not having a dicamba-resistant trait. Crop plants that are not susceptible to certain auxin herbicides, such as corn, or plants having the dicamba-resistant trait typically have no pre-planting restriction and the formulations of the present invention can be applied immediately before planting such crops.

The formulations of the present invention can be applied at planting or post-emergence to crop plants having a dicamba-resistant trait to control auxin-susceptible weeds in a field of the crop plants and/or adjacent to a field of the crop plants. The formulations of the present invention can also be applied post-emergence to crop plants and/or adjacent to crop plants not having a dicamba resistant trait, such as corn, but that are not susceptible to auxin herbicides.

As used herein, "prior to planting of the crop plant" refers, for example, to a time period of from about 40 days prior to planting of the crop plant to immediately before planting of the crop plant, from about 35 days prior to planting of the crop plant to immediately before planting of the crop plant, from about 30 days prior to planting of the crop plant to immediately before planting of the crop plant, from about 25 days prior to planting of the crop plant to immediately before planting of the crop plant, from about 20 days prior to planting of the crop plant to immediately before planting of the crop plant, from about 15 days prior to planting of the crop plant to immediately before planting of the crop plant, from about 10 days prior to planting of the crop plant to immediately before planting of the crop plant, or from about 5 days prior to planting of the crop plant to immediately before planting of the crop plant. "Preemergence to the crop plant" refers to anytime during the interval from planting of the crop plant up to, but not including, emergence of the crop plant (i.e., before cracking). For example, during the interval of from about 1 day after planting, from about 2 days after planting, from about 3 days after planting, from about 4 days after planting, from about 5 days after planting, from about 10 days after planting, from about 15 days after planting, or from about 20 days after planting of the crop plant up to, but not including, emergence of the crop plant.

As noted, the formulations of the present invention can also be applied to the field postemergence to the crop plant. "Post emergence to the crop plant" refers to anytime during the interval from emergence of the crop plant (i.e. cracking) up to about 1 day after emergence, up to about 2 days after emergence, up to about 3 days after emergence, up to about 4 days after emergence, up to about 5 days after emergence, up to about 10 days after emergence, up to about 15 days after emergence, or up to about 20 days after emergence of the crop plant.

The formulations of the present invention can also be applied preemergent to the weeds. Applying preemergent to the weeds generally refers applying the formulation at any time during an interval from about 40 days, from about 30, from about 25 days, from about 20 days, from about 15 days, from about 10 days, or from about 5 days preemergence of the weeds.

The formulations of the present invention may also be applied postemergent to the weeds. Applying the formulations postemergent to the weeds generally refers to applying the formulation at any time during an interval up to about 1 day after emergence, up to about 2 days after emergence, up to about 3 days after emergence, up to about 4 days after emergence, up to about 5 days after emergence, up to about 10 days after emergence, up to about 15 days after emergence, or up to about 20 days after emergence of the weeds.

In various embodiments, the weeds comprise one or more glyphosate-resistant species and the formulation comprises dicamba. In various other embodiments, the weeds comprise one or more dicamba-resistant species and the formulation further comprises glyphosate.

Weed control mentioned herein refers to any observable measure of control of plant growth, which can include one or more of the actions of (1) killing, (2) inhibiting growth, reproduction or proliferation, and (3) removing, destroying, or otherwise diminishing the occurrence and activity of plants. Weed control can be measured by any of the various methods known in the art. For example, weed control can be determined as a percentage as compared to untreated plants following a standard procedure wherein a visual assessment of plant mortality and growth reduction is made by one skilled in the art specially trained to make such assessments. In another control measurement method, control is defined as a mean plant weight reduction percentage between treated and untreated plants. In yet another control measurement method, control can be defined as the percentage of plants that fail to emerge following a preemergence herbicide application. A "commercially acceptable rate of weed control" varies with the weed species, degree of infestation, environmental conditions, and the associated crop plant. Typically, commercially effective weed control is defined as the destruction (or inhibition) of at least about 60%, 65%, 70%, 75%, 80%, or even at least 85%, or even at least 90%. Although it is generally preferable from a commercial viewpoint that 80-85% or more of the weeds be destroyed, commercially acceptable weed control can occur at much lower destruction or inhibition levels, particularly with some very noxious, herbicide-resistant plants. Advantageously, the herbicidal microcapsules used in accordance with the present invention achieve commercially acceptable weed control in the time period of from application of the herbicide microcapsules, for example as contained in an application mixture, to 3 weeks, 4 weeks, 5 weeks, 6 weeks, 7 weeks, 8 weeks, 9 weeks, 10 weeks, 11 weeks, or even 12 weeks after application of the herbicide microcapsules.

Crop damage can be measured by any means known in the art, such as those described above for weed control determination. A "commercially acceptable rate of crop injury" for the present invention likewise varies with the crop plant species. Typically, a commercially acceptable rate of crop injury is defined less than about 20%, 15%, 10% or even less than about 5%. The herbicidal microcapsules and methods of the present invention limit crop injury to a commercially acceptable rate as measured from about 24 hours (about 1 Day After Treatment or DAT) after application to two weeks (about 14 DAT), from about 24 hours (about 1 DAT) after application to three weeks (about 21 DAT), or from about 24 hours (about 1 DAT) to about four weeks (about 28 DAT).

Having described the invention in detail, it will be apparent that modifications and variations are possible without departing from the scope of the invention defined in the appended claims.

EXAMPLES

The following non-limiting examples are provided to further illustrate the present invention.

Example 1

The following example describes adsorption of dicamba onto silica and organoclays along with various cationic salts. Spray solutions (suspensions) were formed by mixing the silica/organoclay, dicamba, and alkyl cations and dicamba adsorption was tested by measuring the dicamba content of the supernatant. The supernatant was recovered using a filter (pore size 0.2 μm) and a syringe or centrifuging the suspension at 12,000 revolutions per minute (rpm) for approximately 10 minutes. The diglycolamine salt of dicamba (DGA) was utilized as the source of dicamba ions.

TABLE 1

| No. | DGA Dicamba (wt %) | Particulate Silica/Content (wt %) | Organiccation/Content (wt %) | Adsorption (wt %) |
|---|---|---|---|---|
| 1 | 1.2 | Aerodisp W341 (0.6) | BKC (1.9) | 60.0 |
| 2 | 1.2 | Aerodisp W341 (2.4) | BKC (1.9) | 72.0 |
| 3 | 1.2 | Optigel-OGCK (1.2) | HdTAB (2.0) | 41.6 |
| 4 | 1.2 | Optigel-OGCK (2.4) | HdTAB (2.0) | 53.2 |
| 5 | 1.2 | Optigel-OGCK (2.4) | DTMAC (1.45) | 47.8 |
| 6 | 1.2 | Aerodisp W7330N (2.4 wt %) | DTMAC (1.45 wt %) | 12.7 |
| 7 | 1.2 | Montmorrilonite K 10 (2.4) | HdTAB (2.0) | 30.2 |
| 8 | 1.2 | Optigel-OGCK (1.2) Montmorrilonite K 10 (1.2) | HdTAB (2.0) | 32.8 |
| 9 | 1.2 | Montmorrilonite K 10 (2.4) | DTMAC (1.45) | 21.3 |
| 10 | 1.2 | Optigel-OGCK (2.4) | TBMAC (1.2) HdTAB (1.2) | 26.2 |
| 11 | 1.2 | Optigel-OGCK (2.4) Aerodisp W7330N (1.2 wt %) | HdTAB (2.0) | 38.4 |
| 12 | 1.2 | Optigel-OGCK (2.4) | TEAC (1.04) | 20.5 |

Sorbents:
Organoclays: Optigel-OGCK; Montmorrilonite K 10
Fumed silicas: Aerodisp W341; Aerodisp W7330N
Cations:
BKC: Benzalkonium chloride
HdTAB: hexadecyl trimtehylammonium bromide
DTMAC: Dodecyltrimethylammonium chloride
TEAC: tetratethyl chloride
TBMAC: tributylmethylammonium chloride These results indicate suitable adsorption of dicamba onto particulate silicas and organoclays, with particularly advantageous adsorption performance for particulate silicas.

Example 2

The following example details testing the residual effect of dicamba formulations prepared as described above in the form of spray solutions, and containing 1.2 wt. % dicamba (a.e.) during greenhouse testing.

TABLE 2

| Name (Product, NBP # or MON #) | Salt type | Active amt, % ae or ai by mass | Comp 1 | amt 1 | Comp 2 | amt 2 |
|---|---|---|---|---|---|---|
| 08508352-2 | DGA | 1.2% | DTMAC | 1.45% | Clay | 2.4% |
| 08508352-3 | | 1.2% | HdTAB | 2.00% | (Optigel-OGCK) | 1.8% |
| 08508352-4 | | 1.2% | HdTAB | 2.00% | | 1.2% |
| 08508354-16 | | 1.2% | DTMAC | 1.45% | Silica | 2.4% |
| 08508355-20 | | 1.2% | DTMAC | 1.45% | Clay (Mont. K10) | 2.4% |
| 08508355-22 | | 1.2% | HdTAB | 2.00% | Clay | 1.2% |
| 08508357-30 | | 1.2% | TEAC | 1.04% | (Optigel-OGCK) | 2.4% |
| 08508360-8 | K | 1.2% | HdTAB | 2.00% | | 2.4% |
| 08508360-9 | DGA | 1.2% | Benzalkonium chloride | 1.80% | Silica | 2.4% |

The control sample for the testing was commercially available CLARITY (BASF) which contains 56.8 wt % active ingredient (a.i.) (38.5 wt % a.e.) of the diglycolamine (DGA) salt of dicamba.

Figure 1:
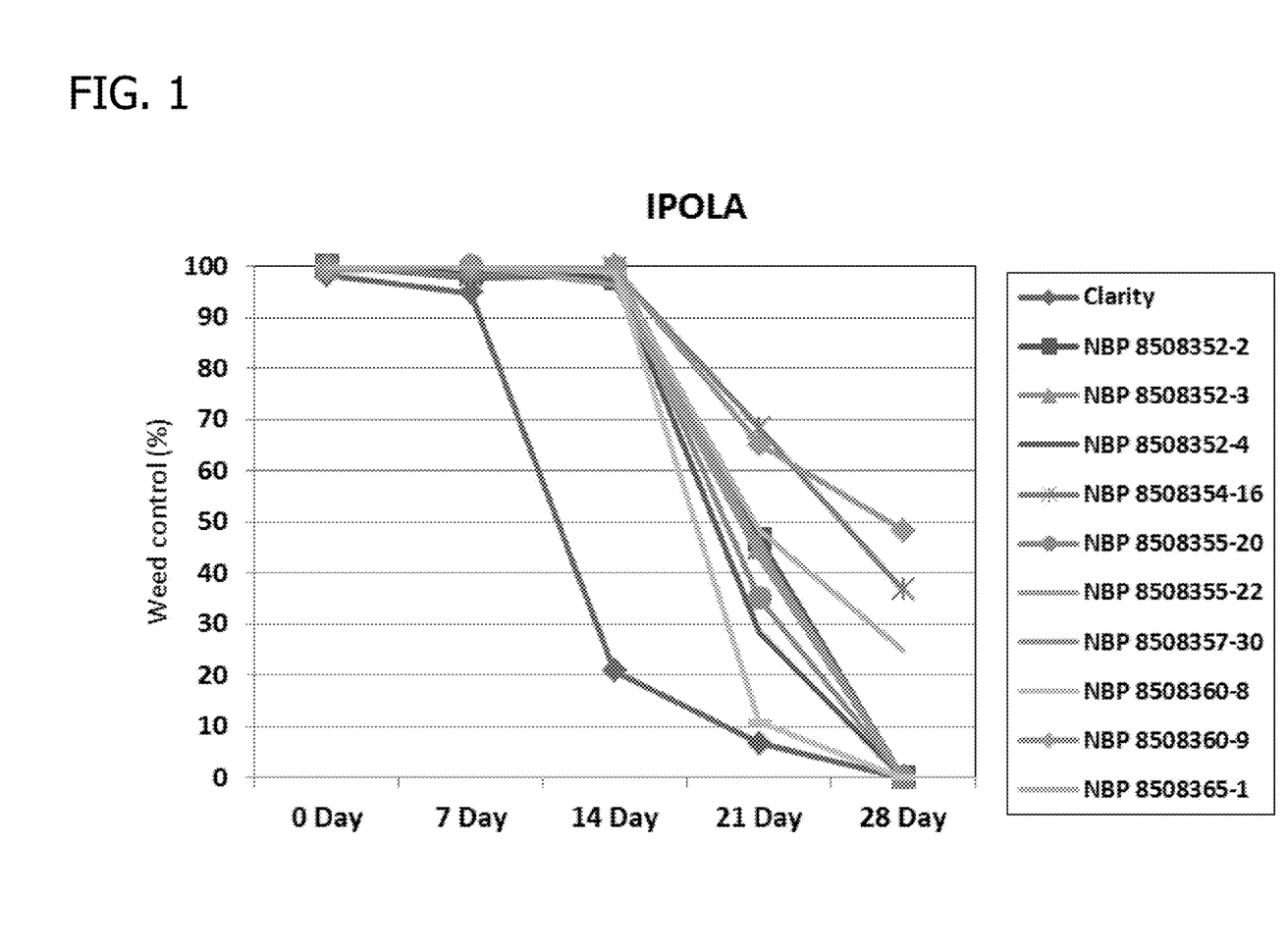
FIG. 1 displays testing results as described in Example 2.

Formulations from Table 2 and CLARITY were sprayed over soil to investigate the residual effect of the compositions of the present invention. The formulations were applied at rates of 450 g a.e./a in the equivalent of 10 gallons/a of water. The results at 0, 7, 14, 21, and 28 days after treatment (DAT) are shown in Table 3. FIG. 1 displays the results of the residual testing graphically.

TABLE 3

| IPOLA | 0 Day | 7 Day | 14 Day | 21 Day | 28 Day |
|---|---|---|---|---|---|
| Clarity | 98.2 | 94.7 | 20.8 | 6.7 | 0.0 |
| NBP 8508352-2 | 100.0 | 98.5 | 97.7 | 46.7 | 0.0 |
| NBP 8508352-3 | 99.7 | 100.0 | 100.0 | 45.0 | 0.0 |
| NBP 8508352-4 | 100.0 | 97.7 | 98.2 | 28.3 | 0.0 |
| NBP 8508354-16 | 100.0 | 98.0 | 99.3 | 68.3 | 36.7 |
| NBP 8508355-20 | 100.0 | 100.0 | 99.7 | 35.0 | 0.0 |
| NBP 8508355-22 | 99.7 | 100.0 | 96.3 | 43.3 | 0.0 |
| NBP 8508357-30 | 100.0 | 100.0 | 99.7 | 43.3 | 0.0 |
| NBP 8508360-8 | 99.8 | 100.0 | 99.0 | 10.8 | 0.0 |
| NBP 8508360-9 | 99.2 | 100.0 | 99.5 | 65.0 | 48.3 |
| NBP 8508365-1 | 99.8 | 100.0 | 98.8 | 48.3 | 25.0 |

As shown in the testing results, dicamba formulations of the present invention provided greater residual effect than CLARITY.

Example 3

The following example details greenhouse testing for residual performance for (1) a composition prepared in accordance with the present invention and (2) a commercially available dicamba herbicide (CLARITY).

The composition of the present invention was in the form of an aqueous suspension and had the following composition: DGA dicamba (approx. 16 wt %), Aerodisp WK 341 (fumed silica particles) (approx. 17 wt %), and benzalkonium cations (approx. 16 wt %).

Two tests were conducted comparing efficacy (% control) over the course of 28 days.

Figure 2:
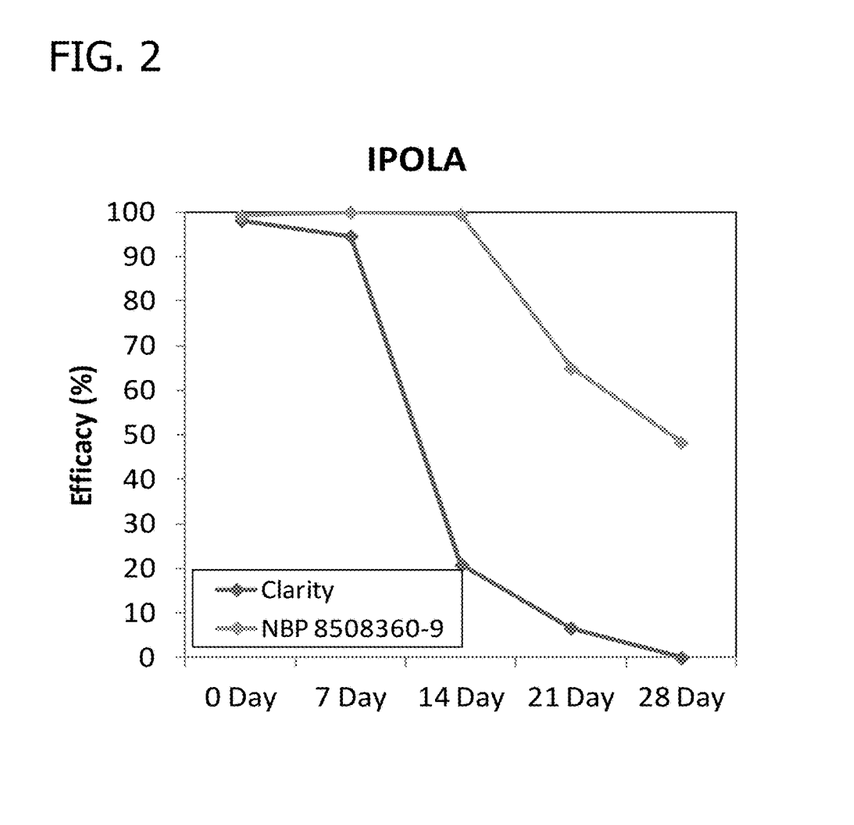
FIGS. 2 and 3 display testing results as described in Example 3.

For Test 1, the formulations were applied at rates of 450 g a.e./a and residual effect was tested at 0, 7, 14, 21, and 28 days. The results are shown in FIG. 2. As shown, the dicamba formulations of the present invention provided greater residual control during each testing interval.

Figure 3:
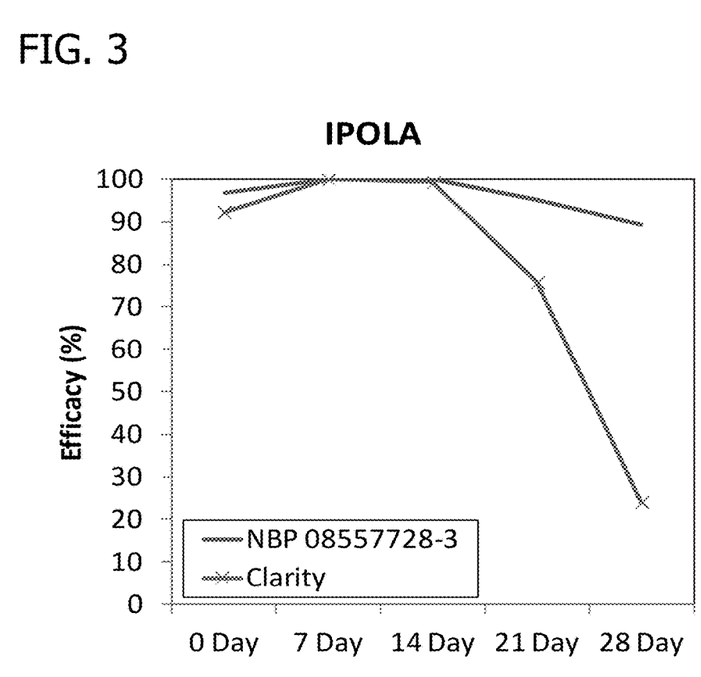

For Test 2, the formulations were applied at rates of 450 g a.e./a and residual effect was tested at 0, 7, 14, 21, and 28 days. The results are shown in FIG. 3. As shown, the dicamba formulations of the present invention provided improved residual control.

Example 4

This example details the results of volatility testing for herbicidal formulations prepared in accordance with the present invention including organic cations and an anionic herbicide. Volatility reduction was determined using either the "Tube" or "Humidome" method (each detailed below).

Tube Method

Equipment: Polyurethane Foam (PUF) plug approximately 22 mm×30 mm available from SKC Inc., cat. No. CPM100108-003; 50 mL PET, Centrifuge tube, Corning catalog No. 430290, with a hole drilled into the wall app. ½ inch above the 20 mL line on the tube with a ⅛ inch drill bit; Glass tube to hole the PUF app. 30 mm iD with a nipple on one end to attach to a Tygon Tube; Ring Stand; Parafilm; Air Pump; Constant Humidity/temperature chamber, such as a growth chamber or Incubator; Dicamba/glyphosate solutions.

Procedure: The procedure took place in a growth chamber at a temperature of 35° C. and relative humidity of 40%. A PUF was placed into the glass tube. The top of the tube was wrapped with parafilm such that it would fit snuggly into the top of the centrifuge tube. 10 mL of the dicamba/glyphosate solutions described below to be approximately 2% a.e. dicamba and approximately 6% a.e. glyphosate was placed into the centrifuge tube. The tube was attached to the ring stand and held in a vertical position. The glass tube was fitted into the top of the centrifuge tube. A tygon tube was connected to the nipple on the glass tube. This tube was connected to an air pump through a needle valve to control the air flow at 2 liters per minute (about 0.2 L air/min-mL sample). The air pump was started and air pulled through the tube for 24 hours. After 24 hours, the pump was turned off and the PUF removed from the glass tube. The PUF was placed into 20 mL of methanol to extract the dicamba. The amount of dicamba was quantified by LC/Mass Spectrometric analysis.

Percent volatility reductions for the dicamba/glyphosate formulations of the present invention as compared to Control formulations are shown below.

Humidome Method

In a further set of experiments, dicamba/glyphosate solutions were tested for concentration in the gas phase (air) through air sampling while being exposed to constant temperature and humidity in humidome in growth chambers.

Humidomes were purchased from Hummert International (Part Nos 14-3850-2 for humidomes and 11-3050-1 for 1020 flat tray) and modified by cutting a 2.2 centimeter (cm) diameter hole on one end approx 5 cm from the top to allow for insertion of glass air sampling tube (22 mm OD) containing a polyurethane foam (PUF) filter. The sampling tube was secured with a Viton o-ring on each side of the humidome wall. The air sampling tube external to the humidome was fitted with tubing that was connected to a vacuum manifold immediately prior to sampling.

Dicamba/glyphosate solutions described below were introduced into the humidome by filling the flat tray beneath the humidome with 1 liter of sifted dry or wet 50/50 soil (50% Redi-Earth and 50% US 10 Field Soil) to a depth of about 1 cm and solutions (20 mL) were sprayed over the soil using a track sprayer at a rate of 10 gallons per acre (GPA). To avoid contamination of the sides of the flat tray each tray was nested in an empty tray prior to spraying. In some evaluations, potted soybean or velvetleaf plants were placed on top of the soil.

The flat tray bottom containing the dicamba/glyphosate formulation in a petri dish or on soil was covered with a humidome lid and the lid was secured with clamps. The assembled humidomes were placed in a temperature and humidity controlled environment and connected to a vacuum manifold through the air sampling line. Air was drawn through the humidome and PUF at a rate of 2 liters per minutes (LPM) for 24 hours at which point the air sampling was stopped. The humidomes were then removed from the controlled environment and the PUF filter was removed. The PUF filter was extracted with 20 mL of methanol and the solution was analyzed for dicamba concentration using liquid chromatography-mass spectroscopy methods known in the art. The reported results are an average of 3-6 samples, with typically an average of 4 samples reported.

Percent volatility reductions for certain solutions versus a Control sample are reported below.

The results are set forth in the following tables, which also include details regarding the control samples utilized for the determination of percent volatility reduction.

| NBP | Composition of testing solutions | Volatility reduction compared to Clarity (%) | |
|---|---|---|---|
| | | Tube | Humidome |
| 8503306 (Control 4) | 0.5% ae Dicamba from Clarity with + 1.5% ae glyphosate from MON 78623 + 0.6% Dodecyltrimethylammonium chloride pH 4.17 | 65 | |

| | | | |
|---|---|---|---|
| 8503306 (Control 4) | 0.5% ae Dicamba from Clarity with + 1.5% ae glyphosate from MON 78623 + 0.77% cetylpyridinium chloride pH 4.17 | 65 | |

| | | | |
|---|---|---|---|
| 8508400 (Control 1) | 2% ae Dicamba from Clarity + 6% glyphosate ae from MON 78623 + 2.1% 1-methyl-3-octylimidazolium chloride pH 4.12 | 80 | |

| | | | |
|---|---|---|---|
| 8744505 (Control 5) | 1.2% ae Dicamba from Clarity + 2.4% ae glyphosate from WeatherMAX + 1.0% Benzalkonium chloride pH 4.6 | 75 | | n = 7-17

| NBP | Composition of testing solutions | Volatility reduction compared to Clarity (%) | |
|---|---|---|---|
| | | Tube | Humidome |
| 8744506 (Control 5) | 1.2% ae Dicamba from Clarity + 2.4% ae glyphosate from WeatherMAX + 3.2% Benzalkonium chloride pH 4.6 | | 92 |

| Control 1 | 2% Dicamba ae from Clarity + 6% glyphosate ae from MON 78623 (K glyphosate) pH 4.08 |
| Control 4 | 0.5% Dicamba ae from Clarity with + 1.5% ae glyphosate from MON 78623 pH 4.11 |
| Control 5 | 1.2% ae Dicamba from Clarity + 2.4% ae glyphosate from WeatherMAX pH 4.6 |

Example 5

This example details dicamba leaching in soil for a DGA dicamba formulation prepared in accordance with Example 1 and a commercially available CLARITY (1.2 wt % DGA dicamba) formulation. The formulation of Example 1 contained 1.2 wt % DGA dicamba, 1.8% fumed silica (AERODISP W 7330 N), and 1.8 wt % benzalkonium cations.

Figure 4:
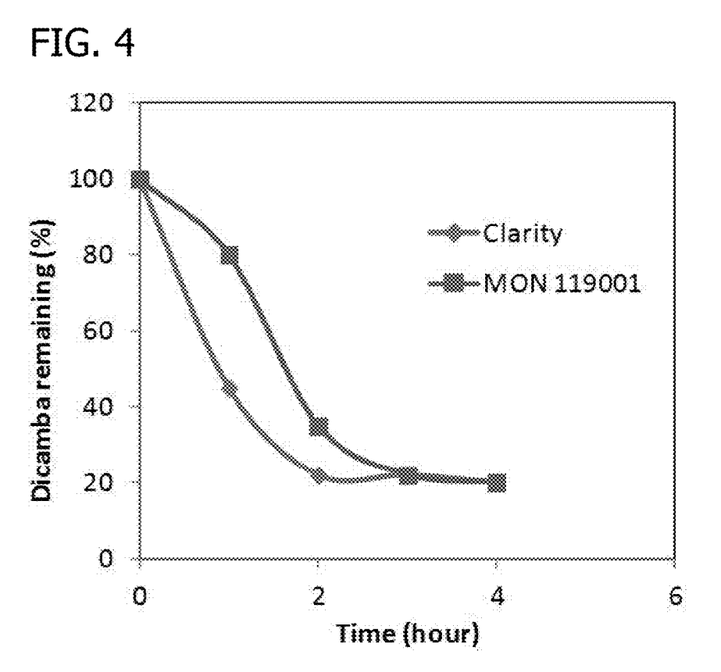
FIG. 4 displays soil leaching testing results as described in Example 5.

A plastic column was packed with a layer of soil that had been dried and screened to a depth of 10 cm. The packed soil was then moisturized by placing a 2 cm layer of water on the soil surface, which was allowed to drain through the soil. After the water drained through the soil, a 30 µl solution containing 1.2% a.e. dicamba (Example 1 and CLARITY) was applied to the top of the soil surface and water was continuously added to the column at a flow rate of 0.1 ml/minute for 8 hours using an HPLC pump for a total water addition of 24 ml. After all was added to the column, water addition was discontinued and the water was allowed to elute from the column and eluted samples were collected every hour over 4 hours and each eluted sample collected was analyzed to determine the dicamba content. The results are shown in FIG. 4.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying Figures shall be interpreted as illustrative and not in a limiting sense.

What is claimed is:

1. An aqueous herbicidal formulation, the formulation comprising:
   dicamba, a particulate sorbent, and a cationic surfactant, wherein:
   the cationic surfactant is bonded to the particulate sorbent and dicamba is bonded to the cationic surfactant bound to the particulate sorbent,
   the particulate sorbent has a silica content of at least 90 wt. %,
   the concentration of dicamba is at least 0.1 wt % acid equivalent (a.e.) relative to the total weight of the formulation,
   the molar ratio of the cationic surfactant to the dicamba is from about 1:1 to about 4:1,
   and the cationic surfactant bound to the particulate sorbent is present in a proportion of at least $1\times10^{-4}$ moles per gram of the particulate sorbent,
   and wherein the cationic surfactant comprises quaternary alkyl ammonium ions of the formula (I):

wherein $R^1$, $R^2$, $R^3$, and $R^4$ are hydrocarbyl or substituted hydrocarbyl having from 1 to 25 carbon atoms.

2. The formulation of claim 1 wherein the particulate sorbent has a silica content of at least 95 wt. %.

3. The formulation of claim 1 wherein the cationic surfactant bonded to the particulate sorbent forms a micelle and dicamba anions are bound to the micelle structure.

4. The formulation of claim 3 wherein the micelle structure includes hydrophobic moieties of the cationic surfactant bound together.

5. The formulation of claim 1 comprising the monoethanolamine, diethanolamine, sodium, potassium, isopropylamine, diglycolamine or dimethylamine salt of dicamba, or a combination thereof.

6. The formulation of claim 5 comprising the monoethanolamine, diethanolamine or potassium salt of dicamba, or a combination thereof.

7. The formulation of claim 5 comprising the diglycolamine salt of dicamba.

8. The formulation of claim 1 wherein the particulate sorbent has a BET surface area of from about 90 to about 300 m²/g.

9. The formulation of claim 1 wherein the particulate sorbent has a negative charge at a pH of from about 2 to about 3.

10. The formulation of claim 1 wherein the dicamba is present at a concentration of from about 10 to about 30 wt. % a.e. relative to the total weight of the formulation.

11. The formulation of claim 1 wherein the dicamba is present in a proportion of from about 300 to about 450 g a.e./l.

12. The formulation of claim 1 wherein the formulation has a pH of from about 2 to about 10.

13. The formulation of claim 1 wherein the molar ratio of the cationic surfactant to the dicamba is from about 1:1 to about 2:1.

14. The formulation of claim 1 wherein $R^1$ is a hydrocarbyl or substituted hydrocarbyl having from 5 to 25 carbon atoms.

15. The formulation of claim 1 wherein $R^1$ is a hydrocarbyl or substituted hydrocarbyl having from 12 to 20 carbon atoms and $R^2$, $R^3$, and $R^4$ are methyl.

16. The formulation of claim 1 wherein $R^1$, $R^2$, $R^3$, and $R^4$ are ethyl.

17. The formulation of claim 1, the formulation further comprising ions of a second herbicide selected from the group consisting of glyphosate, acetochlor, and combinations thereof.

18. The formulation of claim 17, the formulation further comprising acetochlor.

19. An aqueous herbicidal formulation, the formulation comprising:
   dicamba, a particulate sorbent, and a cationic surfactant, wherein:
   the particulate sorbent has a silica content of at least 90 wt. %;
   the cationic surfactant is bonded to the particulate sorbent and dicamba is bonded to the cationic surfactant bound to the sorbent, the formulation further comprising glyphosate;
   wherein the molar ratio of the cationic surfactant to the dicamba is from about 1:1 to about 4:1, and the cationic surfactant bound to the particulate sorbent is present in a proportion of at least $1\times10^{-4}$ moles per gram of the particulate sorbent,
   and wherein the cationic surfactant comprises quaternary alkyl ammonium ions of the formula (I):

wherein $R^1$, $R^2$, $R^3$, and $R^4$ are hydrocarbyl or substituted hydrocarbyl having from 1 to 25 carbon atoms.

20. A method for controlling weeds in a field of crop plants, the method comprising:
   applying an aqueous herbicidal formulation to the field in an herbicidally effective amount, wherein the aqueous herbicidal formulation is as defined in claim 1.

21. A method for controlling weeds in a field of crop plants, the method comprising:
   applying an aqueous herbicidal formulation to the field in an herbicidally effective amount, wherein the aqueous herbicidal formulation is as defined in claim 19.

* * * * *